(12) United States Patent
Kadiyala

(10) Patent No.: US 7,993,578 B2
(45) Date of Patent: Aug. 9, 2011

(54) METHODS AND KITS FOR ASEPTIC FILLING OF PRODUCTS

(75) Inventor: Sudhakar Kadiyala, Newton, MA (US)

(73) Assignee: DePuy Spine, Inc., Raynham, MA (US)

( * ) Notice: Subject to any disclaimer, the term of this patent is extended or adjusted under 35 U.S.C. 154(b) by 478 days.

(21) Appl. No.: 10/977,658

(22) Filed: Oct. 29, 2004

(65) Prior Publication Data

US 2006/0093513 A1 May 4, 2006

(51) Int. Cl.
- *A61L 2/00* (2006.01)
- *A61L 2/04* (2006.01)
- *A61L 9/00* (2006.01)
- *A61L 11/00* (2006.01)
- *C23F 11/00* (2006.01)

(52) U.S. Cl. .......................................... 422/1
(58) Field of Classification Search ................ 422/1
See application file for complete search history.

(56) References Cited

U.S. PATENT DOCUMENTS

| | | | |
|---|---|---|---|
| 4,882,149 A | 11/1989 | Spector | |
| 5,023,087 A * | 6/1991 | Yau-Young | 424/450 |
| 5,522,155 A | 6/1996 | Jones | |
| 5,596,814 A | 1/1997 | Zingle et al. | |
| 5,674,292 A | 10/1997 | Tucker | |
| 5,724,988 A * | 3/1998 | Dennehey et al. | 600/580 |
| 5,732,837 A | 3/1998 | Jones | |
| 5,824,084 A | 10/1998 | Muschler | |
| 6,028,242 A | 2/2000 | Tucker | |
| 6,049,026 A * | 4/2000 | Muschler | 424/93.7 |
| D425,205 S | 5/2000 | Henigan et al. | |
| D430,939 S | 9/2000 | Zukor et al. | |
| 6,127,143 A * | 10/2000 | Gunasekaran | 435/68.1 |
| 6,333,029 B1 | 12/2001 | Vyakarnam et al. | |
| 6,355,699 B1 | 3/2002 | Vyakarnam et al. | |
| 6,372,494 B1 * | 4/2002 | Naughton et al. | 435/391 |
| 6,468,543 B1 * | 10/2002 | Gilbertson et al. | 424/198.1 |
| 6,800,245 B1 * | 10/2004 | Erbe et al. | 422/1 |
| 2002/0068267 A1 | 6/2002 | Horowitz et al. | |
| 2002/0161449 A1 | 10/2002 | Muschler | |
| 2002/0179537 A1 * | 12/2002 | Sukavaneshvar et al. | 210/723 |
| 2003/0108597 A1 * | 6/2003 | Chancellor et al. | 424/450 |
| 2003/0143258 A1 * | 7/2003 | Knaack et al. | 424/426 |
| 2003/0161816 A1 * | 8/2003 | Fraser et al. | 424/93.7 |
| 2003/0185803 A1 | 10/2003 | Kadiyala | |
| 2003/0220245 A1 * | 11/2003 | Hubbell et al. | 514/12 |
| 2004/0071668 A1 * | 4/2004 | Bays et al. | 424/93.7 |
| 2004/0120849 A1 * | 6/2004 | Stewart et al. | 422/22 |

(Continued)

FOREIGN PATENT DOCUMENTS

EP    1348453 A    10/2003

(Continued)

OTHER PUBLICATIONS

Ijiri S. et al: "Effect of Sterilization on Bone Morphogenetic Protein"; Journal of Orthopaedic Research, The Journal of Bone and Joint Surgery, Inc.; Sep. 1994; pp. 628-636; vol. 12, No. 5; US.

(Continued)

*Primary Examiner* — Sean E Conley
*Assistant Examiner* — Regina Yoo

(57) ABSTRACT

This invention relates to new methods & kits that minimize the risks and challenges associated with sterilization of multi-component medical devices.

17 Claims, 2 Drawing Sheets

U.S. PATENT DOCUMENTS

| | | | |
|---|---|---|---|
| 2004/0143344 A1* | 7/2004 | Malaviya et al. | 623/23.72 |
| 2004/0197373 A1 | 10/2004 | Gertzman et al. | |
| 2005/0058632 A1* | 3/2005 | Hedrick et al. | 424/93.7 |
| 2005/0205498 A1* | 9/2005 | Sowemimo-Coker et al. | 210/782 |
| 2006/0062825 A1* | 3/2006 | Maccecchini | 424/423 |
| 2006/0205652 A1* | 9/2006 | Zamora et al. | 514/12 |

FOREIGN PATENT DOCUMENTS

| | | |
|---|---|---|
| JP | 1988500172 | 1/1988 |
| JP | 1992500817 | 2/1992 |
| JP | 2002515288 | 5/2002 |
| JP | 2003104302 | 4/2003 |
| WO | WO 8607265 | 12/1986 |
| WO | WO 9101135 | 2/1991 |
| WO | 96/40297 A | 12/1996 |
| WO | WO 9800174 | 1/1998 |
| WO | 99/59500 A | 11/1999 |
| WO | 02/40963 A | 5/2002 |
| WO | 02/006810 A | 9/2002 |
| WO | WO 02068010 | 9/2002 |

OTHER PUBLICATIONS

Higuchi, "Cell Separation Between Mesenchymal Progenitor Cells Through Porous Polymeric Membranes", Biomed Mater Res Part B: Appl Biomater, 2005, pp. 511-519, 74B, Wiley Periodicals.

Uriji, "Effect of sterilization on bone morphogenetic protein", J Orthop Res., 1994, pp. 628-636, vol. 12(5)- abstract.

* cited by examiner

METHODS AND KITS FOR ASEPTIC FILLING OF PRODUCTS

BACKGROUND OF THE INVENTION

1. Field of the Invention

This invention is concerned with novel sterilization techniques, particularly with techniques involved with sterilization of multi-component medical device implants of which components have varying degrees of resiliency dependent on the sterilization technique.

2. Related Art

Sterilization is a key step in providing safe and efficacious products, particularly for implantable medical devices.

Currently medical devices are terminally sterilized using a variety of methods, such as ethylene oxide, gamma sterilization. For products that are in a liquid form, sub-micron filters may be used to sterilize the product. However, there are some devices that might require combinations of components that may not be compatible with the same sterilization method. For example, a mixture of a growth factor with a scaffold. In this instance, the two components may be separately sterilized or aseptically processed using the appropriate method and are then brought together aseptically at the final stage of processing. Due to the open nature of the aseptic processing, there is always a chance of contamination, leading to the rejection of the product lot.

Alternately, the combined product may be terminally sterilized, wherein the final product may be sterilized by conventional sterilization techniques such as by ethylene oxide or gamma irradiation. However, terminal sterilization techniques may affect the efficacy or other physical properties of the combined medical device.

Therefore, there is a need for novel methods and devices that are adaptable to sterilizing multiple components that have different degrees of resiliency to sterilization techniques such as may occur when a single terminal sterilization technique is used on a combination of components of a device that may be adequate for one of the components but may destroy the efficacy of the other component(s). One such advance in sterilization techniques is provided for by the invention hereinafter disclosed.

SUMMARY OF THE INVENTION

One embodiment of this invention is directed to a method of sterilization of a multi-component medical device comprising:
 a) providing a carrier in a housing, the housing having a port;
 b) sterilizing the carrier within the housing; and
 c) introducing a biologic agent capable of being filter sterilized through the port for combination with the carrier.

A major advantage of this invention is that medical devices that have components of different resiliencies to particular sterilization techniques may be combined by tailoring the sterilization techniques to a particular component. In this way the susceptibility of one component to lose its strength or efficiency is not compromised by the effects of a single sterilization step for both components.

DETAILED DESCRIPTION OF PREFERRED EMBODIMENTS OF THE INVENTION

Figure 1:
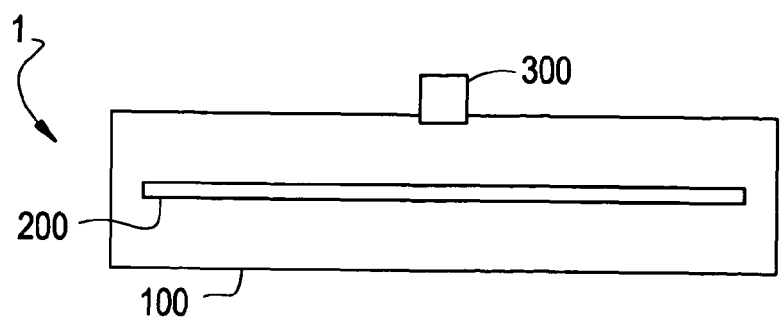
FIG. 1 depicts one embodiment of this invention comprising a housing, a carrier in the housing and an inlet port for introduction of a biologic agent.

One embodiment of the invention is found in FIG. 1. Referring to FIG. 1, the first component (a carrier or scaffold, e.g.) 200 is enclosed in housing 100. Port 300 allows for introduction of the second component. Typically, port 300 will contain a piercable septum to allow introduction of the biologic agent but which prevents entry of contaminates not intended to be introduced. Preferably, port 300 also comprises a micro filter capable of sterilizing the biologic agent (in the event the biologic agent had not been sterilized before hand) and sized to prevent introduction of contaminates such as living microorganisms.

As used herein, the term carrier is intended to encompass items that are capable of carrying a biologic agent. The carrier is not restricted to any particular form and may be embodied as a gel, a non-porous solid, or porous solids such as foams, sponges, and scaffolds, for example.

Figure 2:
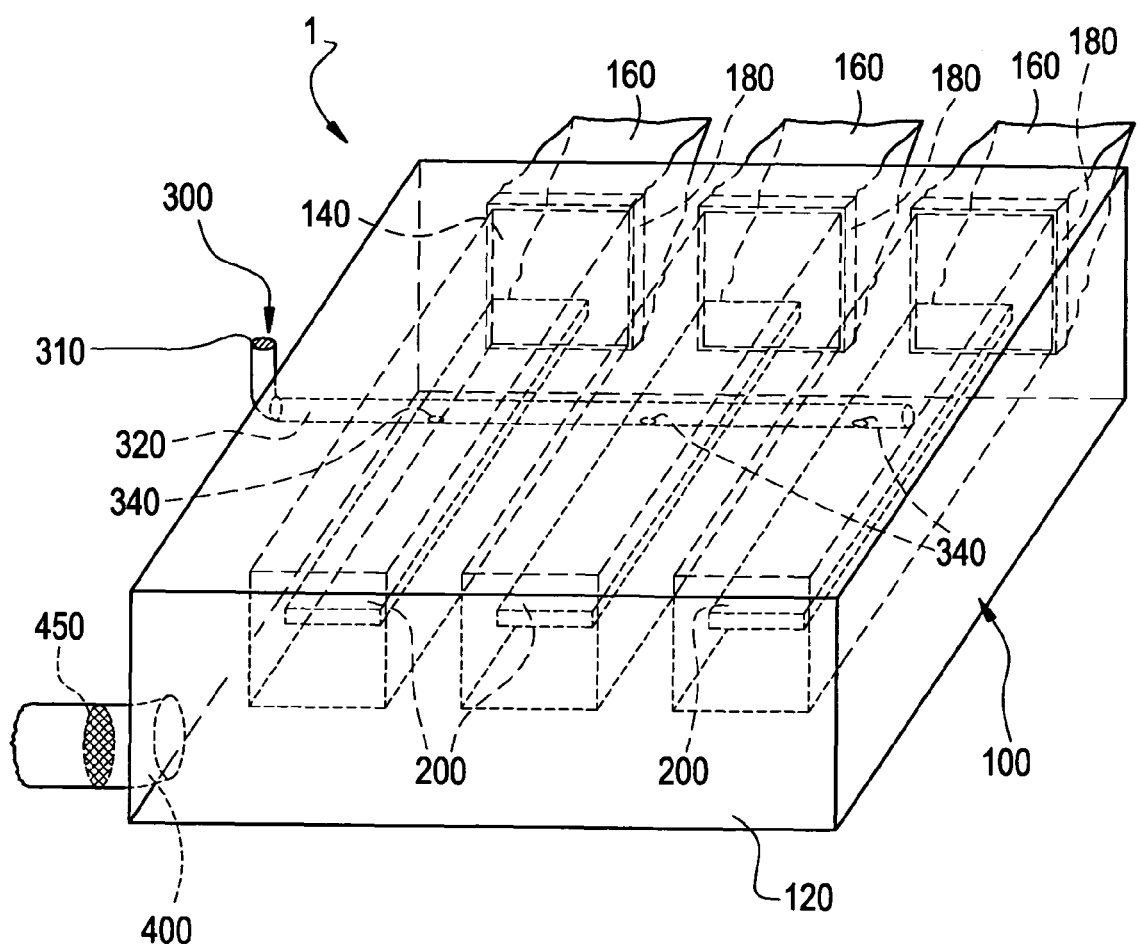
FIG. 2 depicts another embodiment of this invention relating to sterilization of multiple medical devices containing multiple components.

Another embodiment of this invention is depicted in FIG. 2. which shows a kit comprising housing 100 with multiple carriers 200. A biologic agent is introduced to carrier 200 by distribution channel 320 having inlet port 300, equipped with a self-sealing stopper 310 (septum) and distributor sprayers 340 for spraying the biologic agent on the carrier 200. Stopper 310, may optionally comprise a sterilizing filter (0.22 micron pore size) capable of sterilizing the biologic agent as it enters into distribution channel 320. It would be appreciated by those killed in the art that modification to the biologic agent distributor sprayers 340 may be made to impart fine control at multiple locations to provide even and controlled application of biologic agent along the length of carrier 200 as opposed to along the single channel 320 as shown.

FIG. 2 further depicts pouches 160 for accepting the carrier 200 after addition of the biologic agent. Sealable pouches 160 are attached to housing 100 via connection 180. Further, optional perforated member 140 may be present across the cross sectional area of connection 180. Finally exhaust conduit 400 is shown with filter 450. Filter 450 is preferably a sterilizing filter of 0.22 micron pore size.

In operation, with reference to the embodiment of FIG. 2, sterilization of the contents of housing 100 (including the carrier 200 present) is accomplished by e-beam irradiation of the appropriate dose or by any other suitable sterilization technique. Biologic agent is introduced through port 300. If the biologic agent is not sterile, stopper 310 contains a sterilizing filter. The biologic agent is distributed via distribution channel 320 onto carriers 200. If the carriers 200 are not in a lyophilized state, housing 100 is transferred to a freezing unit and frozen. Base 120 of housing 100 is preferably made of a heat conducting material for rapid cooling and heat exchange of housing 100 during lyophilization. After freezing of housing 100 and its contents is complete, a vacuum unit is attached to exhaust 400 to allow evacuation and completion of lyophilization. After completion of lyophilization, housing 100 is tipped and carriers or scaffolds 200 are dropped into pouches 160. Pouches 160 are sealed and then separated from housing 100. Pouches 160 are then suitable for shipping.

Figure 3:
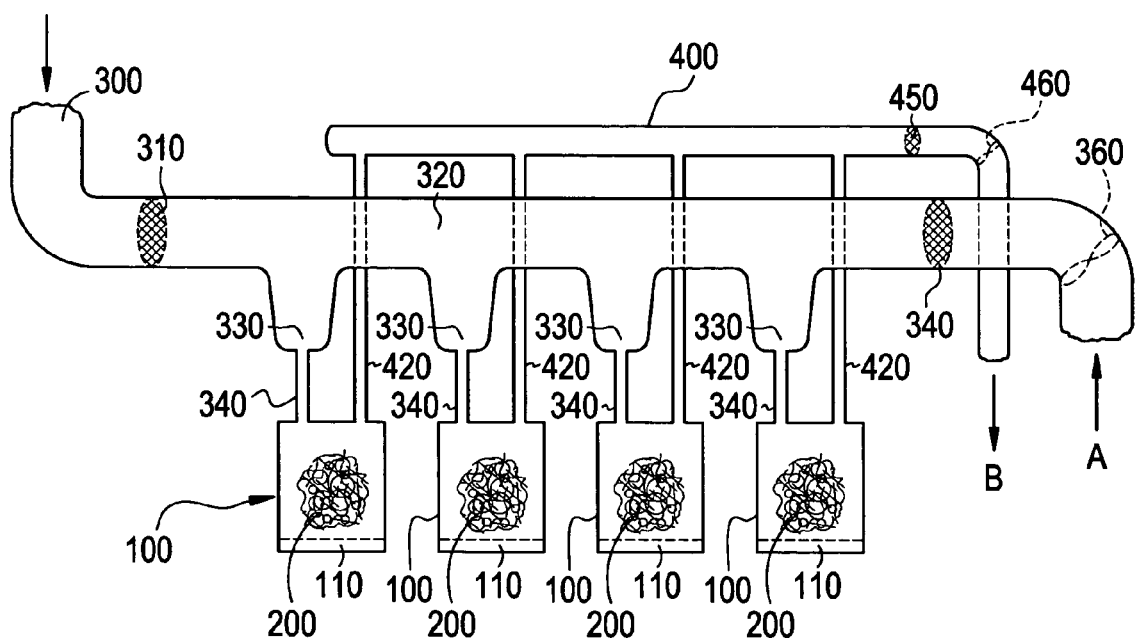
FIG. 3 relates to yet another embodiment of this invention relating to sterilization of multiple medical devices containing multiple components.

Yet another embodiment of this invention is depicted in FIG. 3 and carriers 200 are depicted as sutures. In FIG. 3's embodiment, items 200 are contained in individual housings 100. Housings 100 double as pouches and optionally contain a perforated section 110 for easy opening when the item 200 is intended to be used. FIG. 3 contains distribution manifold 320 having inlet port 300 and filters 310 and 340. Filters 310 and 340 are 0.22 micron filters to prevent biological contamination. Stopcock 360 is also used in operation of this kit as described below. Distribution manifold 320 also contains wells 330 which aid to accumulate and feed the biologic agent through tubes 340 into housing 100. Finally, tubes 420 connect housing 100 to manifold 400 having filter 450 and stopcock 460. Filter 450 is also a 0.22 micron filter to prevent biological contamination.

In operation, ethylene oxide sterilization is used to sterilize the contents 200 in housing 100. Therefore all components in the system at this point should be amenable to ethylene oxide sterilization. The ethylene oxide sterilization may be accomplished under this scenario by first introducing the ethylene oxide at port 300 and allowing it to flow through manifold 320 with stopcock 360 sufficiently opened to permit this while not drawing too much of the flow in order to permit flow of ethylene oxide through pouches 100 and out manifold 400 with stopcock 460 opened. After a sufficient time is allowed for sterilization, stopcocks 460 and 360 are closed.

When the biologic agent is ready to be introduced into the sterilized kit, the agent with any appropriate binder is introduced through port 300 with stopcock 360 open to allows wells 330 to fill with the agent composition. Once the appropriate level of agent is reached in wells 330, stopcock 460 is opened to allow the agent to enter housing 100 and contact item 200. After a sufficient amount of contact time between the agent and item 200 has been reached so as to insure item 200 contains an effective amount of the biologic agent, stopcock 360 is switched to a dry nitrogen source and dry nitrogen enters at point A and flows through the system until all the moisture is driven out through point B. At this stage stopcock 460 is closed and the system pressurized with dry nitrogen to an appropriate pressure. Tubes 340 and 420 leading to each of housing 100 are then sealed using conventional techniques such as by radio-frequency sealing. Individual pouches 100 thus sealed and removed from manifold 320 and 400. Pouches 100 may be placed into another packet and sealed or provided individually for shipping.

While the above embodiments may have been described by a particular sterilization technique for the carrier, one skilled in the art will understand that other sterilization techniques may be used in place of the above demonstrated techniques.

Examples of suitable materials for the carrier include those made of biocompatible materials including those which are non-bioabsorbable (i.e., not able to be readily degraded in the body, whereby the degraded components may be absorbed into or passed out of the body) and bioabsorbable. The biocompatible material may be synthetic or natural.

Examples of synthetic biocompatible materials include but are not limited to polyesters of [alpha]-hydroxycarboxylic acids, such as poly(L-lactide) (PLLA), polyglycolide (PGA), self-reinforced PLLA and self-reinforced PGA; poly-p-dioxanone (abbreviated as PDO or PDS); polyhydroxy acids, poly(ortho esters); poly(beta-hydroxybutyrate) (PHB); poly (PHB-hydroxyvaleric acid), pseudo-poly(aminoacids) or polyiminocarbonates; poly(glycolide-co-trimethylene carbonate); poly-caprolactone (PCL); polyvinyl alcohol (PVA); polyethylene oxide (PEO); polymers disclosed in U.S. Pat. Nos. 6,333,029 and 6,355,699; and any other bioresorbable and biocompatible polymer, co-polymer or mixture of polymers or co-polymers that are utilized in the construction of prosthetic implants (e.g. 85:15 PLLA:PGA, 90:10 PGA: PLLA, or any polymer or co-polymer listed above in combination with a non-degradable material, or any combination of the above at any co-polymer ratio.) In addition, as new biocompatible, bioresorbable materials are developed, it is expected that at least some of them will be useful materials with this invention. It should be understood that the above materials are identified by way of example only, and the present invention is not limited to any particular material.

Natural biocompatible materials are intended to encompass naturally occurring polymers, as well as synthetic modifications or derivatives thereof. Examples of natural biocompatible materials include but are not limited to collagen, recombinant collagen, laminin, elastin, fibronectin, fibrinogen, thrombospondin, gelatin, polysaccharides, poly-1-amino acids, hyaluronic acid, cellulose, alginates, chondroitin sulfate, chitosan, chitin, keratin, silk, small intestine submucosa ("SIS"), and combinations thereof. These materials can be further treated or modified to enhance their mechanical, or degradation or tissue inducing properties by introducing cross-linking agents or changing the hydrophobicity of the side residues or treating with additional components.

Examples of biocompatible, non-bioabsorbable materials include but are not limited to biocompatible metals, including but not limited to stainless steel, cobalt chrome, titanium and titanium alloys; or bio-inert ceramics, including but not limited to alumina, zirconia and calcium sulfate; or non-biodegradable polymers, including but not limited to polyethylene, polyvinyl alcohol (PVA), polymethylmethacrylate (PMMA), silicone, polyethylene oxide (PEO), polyethylene glycol (PEG), and polyurethanes.

A preferred modified and treated collagen based bioabsorbable material is mineralized forms of collagen including HEALOS® mineralized bone graft product available from DePuy Spine, Inc. Another preferred bioabsorbable material is SIS.

Examples of suitable biologic agents are those that have biologic activity and are capable of being filter sterilized and include but are not limited to chemotactic agents; therapeutic agents (e.g., antibiotics, antimicrobials, steroidal and non-steroidal analgesics and anti-inflammatories, anti-rejection agents such as immunosuppressants and anti-cancer drugs); various proteins (e.g., short chain peptides, active or inactive peptides, bone morphogenic proteins, glycoproteins and lipoproteins); cell attachment mediators; biologically active ligands; integrin binding sequence; ligands; various growth and/or differentiation agents (e.g., epidermal growth factor, IGF-I, IGF-II, TGF-$\beta$ I-III, growth and differentiation factors, vascular endothelial growth factors, fibroblast growth factors, platelet derived growth factors, insulin-like growth factor and transforming growth factors), parathyroid hormone, parathyroid hormone related peptide, bFGF; TGF-$\beta$ superfamily factors; bone morphogenetic proteins; BMP-2; BMP-4; BMP-6; BMP-7, BMP-12; sonic hedgehog; GDF5 (also referred to as BMP-14 or MP-52 or rhGDF-5 or CDMP-1); GDF-6; GDF-8; CDMP-2; CDMP-3; PDGF; small molecules or protein equivalents that affect the upregulation of specific growth factors or other processes occurring during a healing response (e.g. TP508 and Chrysalin® both available from OrthoLogic, Tempe, Ariz.); tenascin-C; hyaluronic acid; chondroitin sulfate; fibronectin; decorin; thromboelastin; thrombin-derived peptides; heparin-binding domains; heparin; heparin sulfate; DNA fragments and DNA plasmids as sole constituents or when incorporated into appropriate vectors, such as viral constructs.

Preferably the biologic agent is in liquid form and is filtered sterilized by conventional techniques when introduced through the housing to be combined with the previously sterilized carrier. Such sterilizing filters are available from Millipore, Corporation, Billerica, Mass., USA which provide a large variety of filter having pore sizes of 0.22 microns or less which prevent introduction of living organisms.

Examples of suitable housing materials include but are not limited to polymeric or metallic materials. Preferred polymeric materials include but are not limited to polycarbonates, polyolefin (TYVEK®), polyester (MYLAR®), and polyethylene for example.

EXAMPLES

The following examples are intended as are intended to be illustrative and not limitative of the present invention.

Example 1

A pad of Healos® mineralized collagen bone graft is placed in a polycarbonate housing. The housing is sealed using a water vapor permeable membrane and terminally sterilized using e-beam sterilization. A filter sterilized, buffered-solution containing 0.5 mg/cc rh-GDF-5 is introduced through the membrane onto the Healos® pad. The housing and scaffold with the rh-GDF-5 is then frozen and is ready for shipment to the user site.

Example 2

The same process is followed as in Example 1, except that at the end of the process the housing and the scaffold with the GDF-5 is lyophilized and placed into a vacuum-sealed pouch.

Example 3

The same process is followed as in Example 2, except that the lyophilized package is placed into a sterile mylar outer pouch aseptically.

Example 4

A PLGA foam is placed in a Tyvek® pouch that has a polypropylene tube connected to a 0.22 micron filter. The entire assembly is sterilized using ethylene oxide. A buffered solution containing BMP-2 is introduced into the foam through the filter and then allowed to air dry. The polypropylene tube is then sealed using RF technology to create a sealed housing unit.

Example 5

The same process as in Example 2, except that the housing unit contains two filters. One filter is used for introducing the liquid and a separate one is used for the lyophilization.

It should be understood that the foregoing disclosure and description of the present invention are illustrative and explanatory thereof and various changes in the size, shape and materials as well as in the description of the preferred embodiment may be made without departing from the spirit of the invention.

What is claimed is:

1. A method of sterilization of a multi-component medical device comprising a carrier in a housing, the housing having a port comprising a filter comprising pores no larger than 0.22 microns, the carrier having been sterilized within the housing, and further comprising the step of introducing a solution consisting essentially of a growth factor through the port for combination with the carrier.

2. The method of claim 1, wherein the carrier is a biocompatible carrier.

3. The method of claim 2, wherein the carrier comprises a bioabsorbable material.

4. The method of claim 3, wherein the bioabsorbable material is a synthetic material.

5. The method of claim 4, wherein the synthetic material is selected from the group consisting of polymers and copolymers of polyesters of [alpha]-hydroxycarboxylic acids, poly (L-lactide) (PLLA), polyglycolide (PGA), self-reinforced PLLA, self-reinforced PGA, poly-p-dioxanone, polyhydroxy acids, poly(ortho esters), poly(beta-hydroxybutyrate) (PHB), poly (PHB-hydroxyvaleric acid), pseudo-poly(aminoacids), polyiminocarbonates, poly(glycolide-co-trimethylene carbonate), polycaprolactone (PCL), polyvinyl alcohol (PVA), polyethylene oxide (PEO), and mixtures thereof.

6. The method of claim 3, wherein the bioabsorbable material is a natural material.

7. The method of claim 6, wherein the natural material is selected from the group consisting of collagen, recombinant collagen, laminin, elastin, fibronectin, fibrinogen, thrombospondin, gelatin, polysaccharides, poly-1-amino acids, hyaluronic acid, cellulose, alginates, chondroitin sulfate, chitosan, chitin, keratin, silk, small intestine submucosa ("SIS"), and combinations thereof.

8. The method of claim 1, wherein the housing is selected from the group consisting of polymeric and metallic materials.

9. The method of claim 8, wherein the housing is a polymeric material selected from the group consisting of polycarbonates, polyolefins, polyesters, polyethylenes, and combinations thereof.

10. The method of claim 1, wherein the growth factor is from the TGF-β superfamily.

11. The method of claim 10, wherein the growth factor is a bone morphogenic protein.

12. The method of claim 11, wherein the growth factor is rhGDF-5.

13. The method of claim 11, wherein the growth factor is BMP-2.

14. The method of claim 11, wherein the growth factor is BMP-7.

15. The method of claim 11, wherein the growth factor is GDF-5.

16. The method of claim 15, wherein the carrier is collagen based.

17. The method of claim 15, wherein the carrier is small intestine submucosa.

* * * * *